United States Patent [19]

Beatty

[11] 4,144,740

[45] Mar. 20, 1979

[54] TESTING APPARATUS AND METHOD FOR MEASURING CUTTING, CHIPPING AND ABRASION RESISTANCE

[75] Inventor: James R. Beatty, Akron, Ohio

[73] Assignee: The B. F. Goodrich Company, Akron, Ohio

[21] Appl. No.: 901,933

[22] Filed: May 1, 1978

[51] Int. Cl.$^2$ .............................................. G01N 3/56
[52] U.S. Cl. .......................................... 73/8; 73/104
[58] Field of Search ................. 73/101, 104, 7, 9, 146, 73/12, 8

[56] References Cited

U.S. PATENT DOCUMENTS

| | | | |
|---|---|---|---|
| 2,458,196 | 1/1949 | Phillips | 73/8 X |
| 3,216,238 | 11/1965 | Bailey | 73/7 |
| 3,323,349 | 6/1967 | Savage et al. | 73/7 |

Primary Examiner—Jerry W. Myracle
Attorney, Agent, or Firm—James R. Lindsay

[57] ABSTRACT

A sample of the material to be tested is formed in a disc-shaped specimen and mounted on a spindle inserted in a mounting hole in the specimen. The spindle is rotated about a generally horizontal axis and a single blade cutter is supported above the specimen for dropping on the specimen in cutting engagement therewith. Lifting and dropping is controlled so that there is bouncing of the cutter and repeated engagement of the cutter with the specimen between the lifting and dropping. The diameter of the test specimen is measured before the test and after a predetermined time of the testing. The decrease in diameter is an indication of the cutting and chipping resistance of the material being tested.

16 Claims, 9 Drawing Figures

4,144,740

TESTING APPARATUS AND METHOD FOR MEASURING CUTTING, CHIPPING AND ABRASION RESISTANCE

BACKGROUND OF THE INVENTION

This invention relates generally to testing equipment for testing materials for resistance to cutting, chipping and abrasion. A special need exists for testing of tire tread materials because cutting and chipping of the tread surface of tires has been a problem for many years. The same kind of damage has resulted from the dropping of sharp rocks on a moving belt.

Serious cutting and chipping of the tread surface has been experienced with large off-the-road tires which operate on stone and other rough terrain. A tire of this type costs several thousand dollars and a controlled service performance test of the tire costs a like amount. Considerable time has also been required to perform such a test. Some savings in costs have been obtained by testing the tread materials on smaller truck size tires or in mud and snow treads of passenger tires; however, this has not proven entirely satisfactory as evidenced by the fact these types of tests are not widely used. Also even with the smaller tires, the tire construction and testing entail considerable cost.

Laboratory testing of materials not only saves costs but makes it possible to study many compound variables. Also the time necessary for conducting laboratory tests is considerably shorter. Laboratory tests developed in the past have not been entirely satisfactory in that the results could not always be correlated with the service performance tests and the laboratory testing equipment was difficult to maintain and keep in adjustment.

SUMMARY OF THE PRESENT INVENTION

This invention provides a laboratory cutting and chipping test which predicts service performance with reasonable speed and accuracy. A relatively small sample of the material to be tested in the form of a disc is rotated at a predetermined speed. A single cutter is held over the rotating disc and mounted on a guide so that when the cutter is dropped it will engage the disc. After the cutter engages the disc, it will bounce into and out of cutting engagement with the disc specimen. In addition to cutting the edge surface of the disc the cutter drags along the edge surface between bounces and material is cut and chipped from the surface by the cutter forming a groove in the surface. At regular intervals during the test, the cutter is lifted and dropped on the edge surface of the rotating disc. After a predetermined period of time, the dropping of the cutter and rotation of the disc sample is stopped and the diameter of the groove is measured. This measurement of diameter reduction can then be used to compare the chipping and cutting resistance of the material of the sample with the same properties of other materials.

DESCRIPTION OF THE DRAWINGS

Further objects and advantages of this invention will become apparent from the following description and the accompanying drawings wherein.

DETAILED DESCRIPTION OF THE PREFERRED EMBODIMENT

Figure 1:
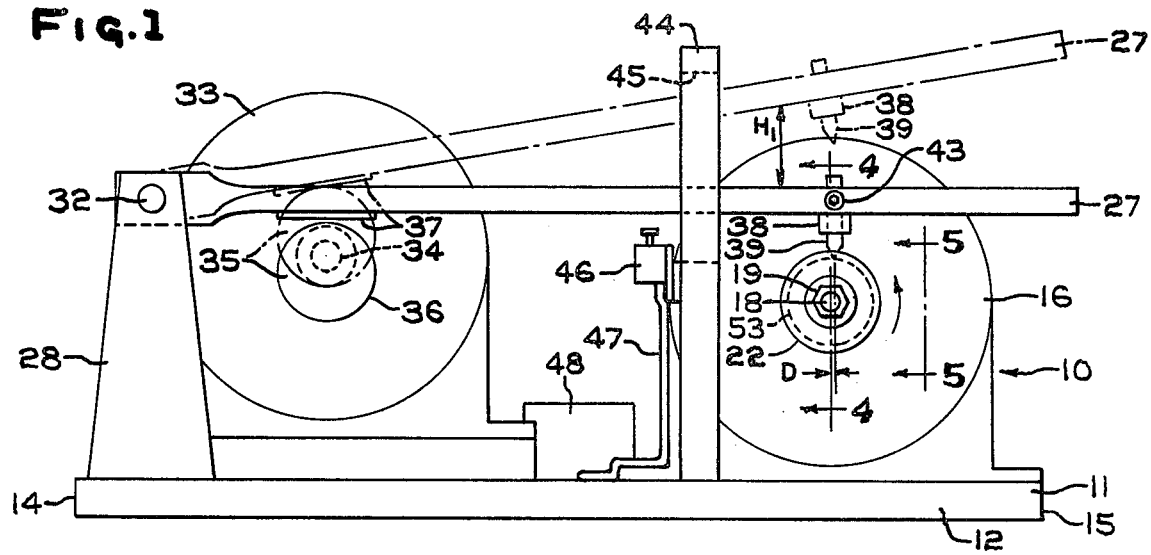
FIG. 1 is an elevation of the testing apparatus embodying the invention with the cutter, circular cam and pivoted beam being shown in the upper lifted position in phantom lines.
Figure 2:
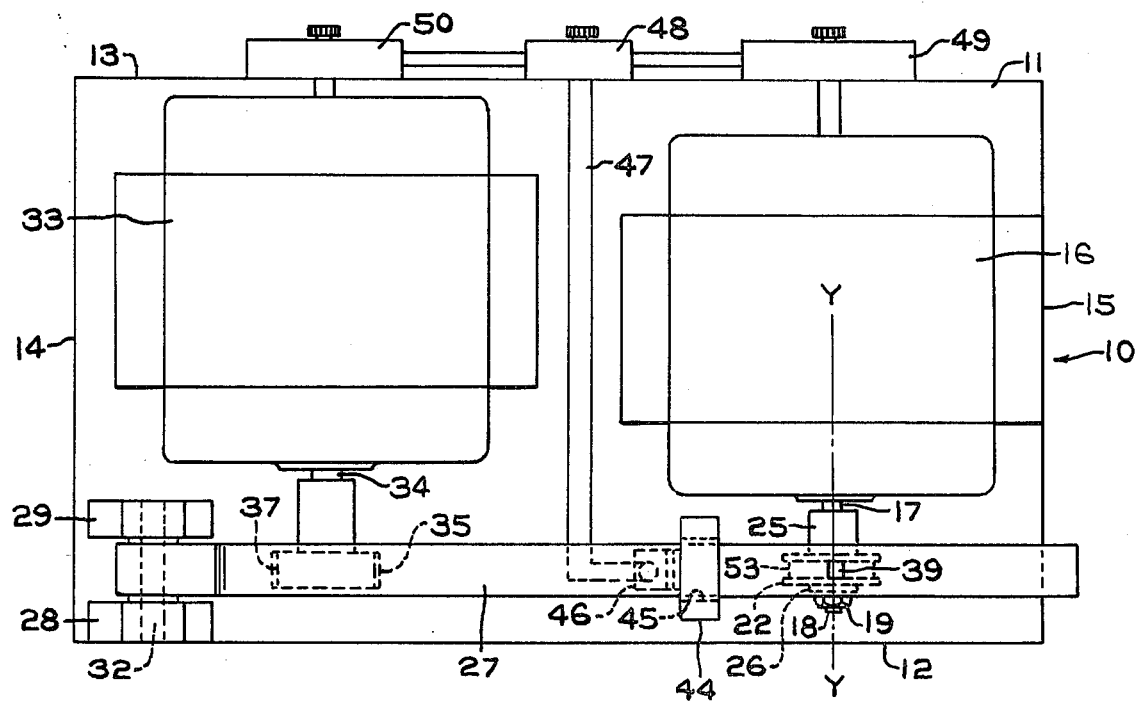
FIG. 2 is a plan view of the apparatus of FIG. 1.
Figure 4:
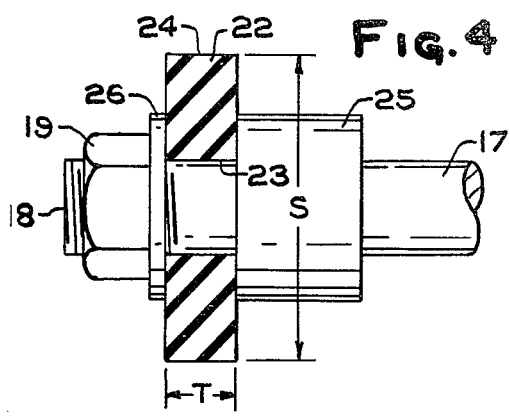
FIG. 4 is an enlarged fragmentary sectional view of the specimen and spindle taken along the plane of line 4—4 in FIG. 1 showing the test specimen mounted on the spindle prior to running of the test.

Referring to FIGS. 1 and 2, a testing apparatus 10 is shown having a base plate 11 which may have a generally rectangular shape with a front edge 12, a rear edge 13, a left side edge 14 and a right side edge 15. Drive means for the testing apparatus 10 may include a specimen driving motor 16 mounted on the right side of the base plate 11 as shown in FIGS. 1 and 2 and having a shaft 17 positioned generally in a horizontal plane and extending in a direction from the front edge 12 to the rear edge 13 and parallel to the right side edge 15 of the base plate. With the base plate 11 in a generally horizontal plane, the shaft 17 is also generally horizontal. At the front end of the shaft 17, there is provided a spindle 18 which may be threaded to receive a nut 19 as shown in FIG. 4. The spindle 18 is a rotatable supporting member for a disc-shaped test specimen 22 which has a central opening 23 for receiving the spindle 18 and a generally cylindrical outer peripheral surface 24. The test specimen 22 is usually of a resilient material and may be a sample from a cured tire or a disc molded from a compound to be tested. The test specimen 22 is held in place on the spindle 18 between a boss 25 on the shaft 17 and a washer 26 interposed between the test specimen and the nut 19.

Extending over the test specimen 22 and spindle 18 and across the front of the base plate 11 is a guide means or beam 27 pivotally mounted between a pair of upright supports such as stanchions 28 and 29 mounted on the base plate at the left front corner as shown in FIGS. 1 and 2. A pivot pin 32 extends in a generally horizontal position and in a direction extending from the front edge 12 to the rear edge 13 and parallel to the left side edge 14 of the base plate 11. The pivot pin 32 extends through aligned openings in the stanchions 28 and 29 and through an opening in the beam 27 which may include bearings to permit ease of swinging motion of the beam in a generally vertical direction about the pivot pin.

On the left side of the base plate 11 as shown in FIGS. 1 and 2, the drive means may further include a beam excitation motor 33 having a shaft 34 extending generally in a direction from the front edge 12 to the rear edge 13 and parallel to the left side edge 14. The shaft 34 is generally horizontal with relation to the base plate 11 which is in a generally horizontal plane when the testing apparatus 10 is in operating condition. A beam lifting means such as a rotatable eccentric circular cam 35 is mounted on the end of the shaft 34 so that the cam surface 36 is in supporting engagement with the beam 27. An insulating member such as a rubber pad 37 may be mounted on the beam 27 to facilitate the operation of the testing apparatus upon rotation of the shaft 34 and lifting of the beam 27 from the lower position shown in full lines in FIG. 1 to the upper position shown in dot-dash lines in FIG. 1.

Figure 3:
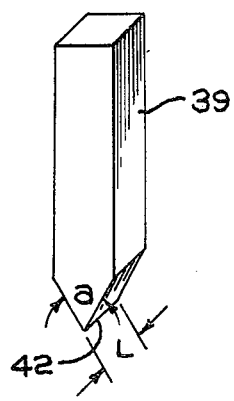
FIG. 3 is an enlarged view in perspective of the cutting tool.

A cutter holder 38 is mounted on the underside of the beam 27 to support a cutting member 39 which in this embodiment is a tool bit of tungsten carbide having a single blade or cutting edge 42 extending generally in a direction from the front edge 12 to the rear edge 13 and parallel to the right side edge 15 of the base plate 11. The cutting member 39 is held in position in the holder 38 on beam 27 by a set screw 43 in the side of the beam. As shown in FIG. 3, the cutting member 39 has a square cross section and the cutting edge 42 has an included angle a of around 60°.

As shown in FIG. 1, the shaft 17 and test specimen 22 are rotated in a counterclockwise direction and the cutting holder 38 is mounted on the beam 27 so that the cutting edge 42 will be spaced to the right of a vertical plane extending through the axis Y—Y of the shaft 17 and spindle 18 with the cutting member 39 in cutting engagement with the outer peripheral surface 24 of the test specimen by an amount D shown in FIG. 1. The offset positioning of the cutting member 39 results in the cutting edge 42 engaging the outer peripheral surface 24 of the test specimen 22 at a portion of the surface which is moving towards the cutting member and thereby assists in the cutting of that surface.

A beam retaining member 44 having a slot 45 through which the beam 27 extends is mounted on the base plate 11 and prevents upward movement of the beam beyond the upper extremity of the slot 45 as shown in FIG. 1. Switch means such as limit switch 46 is mounted on the lower portion of the beam retaining member 44 for engagement by the beam 27 when the cutting member 39 has cut through the test specimen 22 and is in danger of striking the spindle 18. The limit switch 46 is connected to other controls on the testing apparatus by a conduit 47 extending from the limit switch to the rear edge 13 of the base plate 11 on which there may be mounted a timer 48 and speed controls 49 and 50 for the specimen driving motor 16 and the beam excitation motor 33, respectively.

In the preferred embodiment, the shaft 34 of the beam excitation motor 33 is spaced from the pivot pin 32 a distance along the beam 27 sufficient to lift the beam a distance H1 of around 1.85 inches (4.7 centimeters) from the outer peripheral surface 24. The specimen 22 has a diameter S of around 2 inches (5.08 centimeters) and a thickness T of around 0.5 inch (1.27 centimeters). The cutting edge 42 has a length L of around 0.25 inch (0.64 centimeters) and the offset D between the cutting edge and a vertical plane through the axis Y—Y is around 0.1 inch (0.25 centimeters). The specimen 22 is rotated in a counterclockwise direction at a speed of 750 revolutions per minute. The beam excitation motor 33 rotates the cam 35 at 60 revolutions per minute so that the cutting member 39 is dropped into cutting engagement with the test specimen 22 at a frequency of 60 cycles per minute. The weight of the beam 27 and cutting member 39 at the cutting edge 42 is one pound (0.373 kilograms). The frequency of impact is preferably an order of magnitude lower than the natural frequency of the system. This permits damping impacts of decreasing force which appear to simulate the forces causing chipping after the initial cutting. This frequency is a function of the moment of inertia of the system (the beam 27 with the cutter holder 38 and cutting member 39 mounted on it and the damping of the material of the test specimen 22).

The duration of the test should be as short as possible and still provide the desired measurements. With the embodiments shown, ten minutes was sufficient for tread type compounds. The duration of the test may be regulated by the timer 48 which may be set to shut off the specimen driving motor 16 and beam excitation motor 33 at a predetermined time.

The force of impact of the cutting member 39 is an important parameter of this testing apparatus and method. According to calculations using well known formulas, the pressure exerted by the cutting edge 42 on the first impact is approximately 550,000 pounds per square inch (31,801 kilograms per square centimeter). This pressure is believed to be adequate to cause cutting. Subsequent free vibrations or rebounds exert cutting pressures of a reduced magnitude which is a direct function of the resilience of the material of the test specimen 22. With high resilience material, the rebound height is higher so the free-fall distance is greater and the number of cycles of impact increased. This bouncing action of the cutting member 39 which occurs between the intervals of lifting and dropping the beam 27 is believed to be important in measuring the chipping and cutting resistance with this apparatus.

Figure 5:
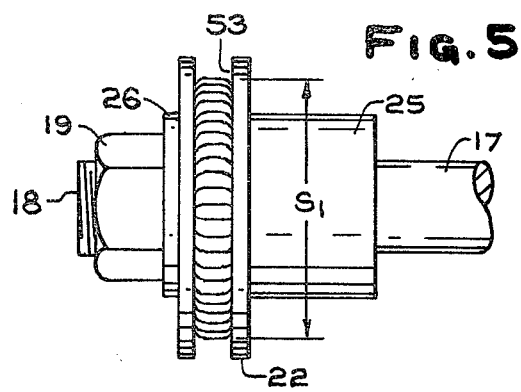
FIG. 5 is an enlarged fragmentary view taken along the plane of line 5—5 in FIG. 1 showing the test specimen after the running of the test.
Figure 6:
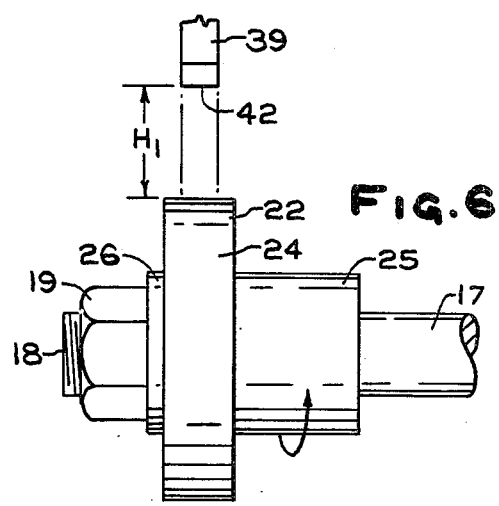
FIG. 6 is a view like FIG. 5 showing the test specimen and cutting tool prior to dropping of the cutting tool.
Figure 7:
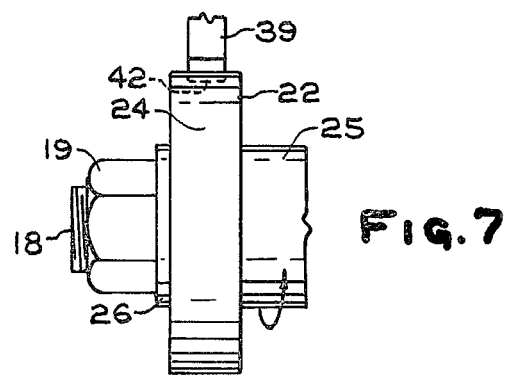
FIG. 7 is a view like FIG. 6 showing the cutting tool when it is first dropped on the specimen and penetrates the peripheral edge.
Figure 8:
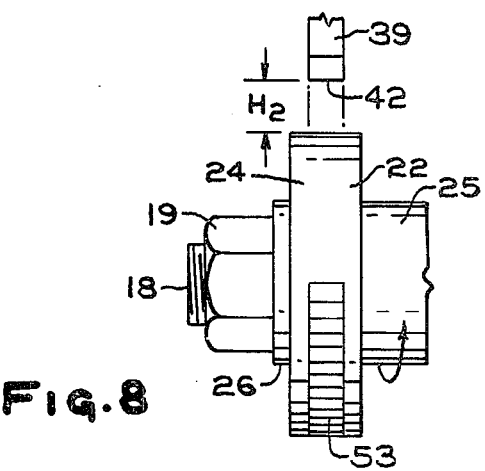
FIG. 8 is a view like FIG. 7 showing the cutting tool in the upper position after it has bounced off the test specimen.
Figure 9:
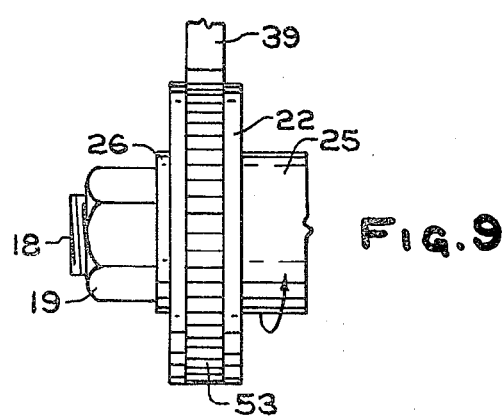
FIG. 9 is a view like FIG. 8 showing the cutting tool after it has dropped from the upper position of FIG. 8 into engagement with the outer peripheral surface of the test specimen.

Referring to FIGS. 6 through 9, a typical action of the cutting member 39 with relation to the test specimen 22 is shown. In FIG. 6, the cutting member 39 is shown in the upper lifted position at a distance H1 of 1.85 inches (4.7 centimeters above the peripheral surface 24 of the specimen 22. This position corresponds with the position of the beam 27 and cutting member 39 shown in dot-dash lines in FIG. 1. FIG. 7 shows the cutting member 39 after it has first dropped on the specimen 22 and the cutting edge 42 has penetrated the outer peripheral surface 24. As shown, the movement of the outer peripheral surface 24 toward the cutting member 39 assists in this cutting action. FIG. 8 shows the cutting member 39 at its uppermost position after bouncing or rebounding from the cutting position shown in FIG. 7. Here the cutting member 39 is at a decreased height H2. FIG. 9 shows the cutting member 39 after it has been dropped from the distance H2 to engage the outer peripheral surface 24 with a lesser impact. This action will continue until the beam 27 is again lifted to the position shown in FIG. 6 and dropped with the cutting member 39 coming into engagement with the outer peripheral surface 24 of the specimen 22. At the end of the testing period, a groove 53 shown in FIG. 5 will be cut in the specimen 22 and have a depth depending upon the cutting and chipping resistance of the material of the test specimen.

A test specimen 22 is tested for cutting and chipping resistance in accordance with the following procedure:

1. The test specimen 22 of a material to be tested is molded in a disc shape or cut from the tread of a tire to a size having a diameter S of 2 inches (5.08 centimeters) and a thickness T of 0.5 inch (1.27 centimeters).

2. The outer peripheral surface 24 of the test specimen 22 is washed with a suitable solvent.

3. Hardness is measured at points 0.25 inch (0.64 centimeters) radially outward from the mounting opening 23 and spaced 90° apart.

4. Each specimen 22 is weighed.

5. The outside diameter of each specimen 22 is initially measured.

6. The specimen 22 is mounted on the spindle 18 and the washer 26 and nut 19 applied to hold the specimen in place against the boss 25.

7. The cutting member 39 is supported above the specimen 22 on the beam 27.

8. The specimen driving motor 16 is started and the speed set at 750 revolutions per minute.

9. The beam excitation motor 33 is started and the speed set at 60 revolutions per minute to provide lifting and dropping of the beam 27 at a frequency of 60 cycles per minute.

10. The timer 48 is set for 10 minutes.

11. At the end of ten minutes both motors 16 and 33 are shut off automatically by the timer 48 and the cutting member 39 lifted from the specimen 22.

12. The test specimen 22 is removed from the spindle 18 by removing the nut 19 and washer 26.

13. The diameter S1 of the groove 53 shown in FIG. 5 is finally measured.

14. The specimen 22 is weighed.

By measuring the decrease in diameter between the diameter S of the specimen 22 before testing and the diameter S1 of the groove 53 cut in the specimen after testing, an indication of the cutting and chipping resistance of the material being tested is obtained.

Although weight loss is measured, it has been found that the diameter loss predicted performance more realistically than did weight loss measurements. It has also been found that the results obtained with this method and testing apparatus 10 in the laboratory correlated with field performance tests. In addition, the apparatus 10 and method met the requirement of test reproducibility in that the variation in results obtained in testing specimens 22 from the same batch of stock was well within the limits required.

With the foregoing disclosure in mind, many and varied obvious modifications of this invention will become readily apparent to those of ordinary skill in the art.

Therefore, what is claimed is:

1. Testing apparatus for measuring the cutting and chipping resistance of a specimen of resilient material comprising a rotatable supporting member for supporting said test specimen for rotation about a generally horizontal axis, drive means for rotating said supporting member and the specimen mounted on the supporting member, a cutting member positioned above said supporting member, lifting means connected to said cutting member for intermittently lifting and dropping said cutting member into cutting engagement with the outer peripheral surface of said specimen, guide means for controlling the movement of said cutting member into and out of engagement with said rotating specimen, and said guide means permitting bouncing of said cutting member on said specimen to repeatedly engage said outer peripheral surface of said specimen during the intervals between the dropping of said cutting member by said lifting means.

2. The testing apparatus of claim 1 wherein said cutting member has a single blade for engaging said specimen.

3. The testing apparatus of claim 2 wherein said blade is of tungsten steel and has an included angle of around 60°.

4. The testing apparatus of claim 1 wherein said rotatable supporting member includes a spindle and said specimen is disc shaped with a central opening for receiving said spindle during mounting of said specimen on said supporting member.

5. The testing member of claim 1 wherein said guide means for controlling the movement of said cutting member includes a beam pivotally supported at one end and connected to said cutting member at a position spaced from said one end so that the weight of said beam will assist in the cutting of said specimen.

6. The testing apparatus of claim 5 wherein said lifting means includes a rotatable eccentric circular cam positioned in supporting engagement under said beam at a position spaced from said one end.

7. The testing apparatus of claim 1 wherein said guide means controls the movement of said cutting member into engagement with a portion of said peripheral surface which is moving towards said cutting member to assist in cutting said surface.

8. The testing apparatus of claim 1 wherein said lifting means is operated at a predetermined speed for lifting and dropping said cutting member at intervals of time great enough to permit bouncing and impacts of decreasing force on said specimen by said cutting member.

9. The testing apparatus of claim 1 wherein said drive means for rotating said supporting member and said lifting means are connected to switch means actuated when said cutting member moves downward beyond a predetermined level to stop the rotation of said specimen and the dropping of said cutting member and thereby protect said apparatus from damage due to cutting away of said specimen to the point where said cutting member engages said supporting member.

10. A method of measuring the cutting and chipping resistance of a disc-shaped test specimen of resilient material comprising initially measuring the outside diameter of said specimen, positioning a cutting member above said specimen, rotating said specimen about a generally horizontal axis at a predetermined speed, intermittently lifting and dropping said cutting member at a predetermined frequency for cutting engagement with the outer peripheral surface of said specimen, stopping the rotation of said specimen and the dropping of said cutting member and finally measuring the outside diameter of said specimen in the area of said peripheral surface engaged by said cutting member to determine the decrease in diameter which is an indication of the cutting and chipping resistance of said material being tested.

11. The method of claim 10 wherein said disc-shaped test specimen is formed from said resilient material to be tested before the outside diameter is initially measured.

12. The method of claim 10 wherein said specimen is mounted on a rotatable supporting member for rotation about a horizontal axis after the outside diameter of said specimen is initially measured.

13. The method of claim 12 wherein the outside diameter of said specimen is finally measured after said specimen is removed from said supporting member.

14. The method of claim 10 wherein said cutting member is guided into and out of bouncing engagement with said specimen after being dropped so that said cutting member will repeatedly engage said outer peripheral surface of said specimen in the intervals between the dropping of said cutting member.

15. The method of claim 10 wherein said cutting member is positioned above said specimen at such a location that said cutting member is dropped on a portion of said outer peripheral surface of said specimen which is moving towards said cutting member to assist in cutting said surface.

16. The method of claim 10 wherein said test specimen has a diameter of around two inches (5.08 centimeters), a thickness of around one-half inch (1.27 centimeters) and is rotated at a speed of 750 revolutions per minute, said cutting member being lifted and dropped at a frequency of 60 cycles per minute from a height of 1.85 inches (4.7 centimeters) and having a cutting edge which has a length of one-quarter inch (0.64 centimeters) and said period of dropping said cutting member and rotating said specimen has a duration of ten minutes.

* * * * *